(12) United States Patent
Ruiz

(10) Patent No.: US 10,194,792 B2
(45) Date of Patent: Feb. 5, 2019

(54) OPTICAL DEVICE, SHEATH AND ENDOTRACHEAL INTUBATION SYSTEM

(75) Inventor: Luis Antonio Ruiz, Guecho (ES)

(73) Assignee: Prodol Meditec S.A., Las Arenas (Vizcaya) (ES)

( * ) Notice: Subject to any disclaimer, the term of this patent is extended or adjusted under 35 U.S.C. 154(b) by 595 days.

(21) Appl. No.: 14/399,718

(22) PCT Filed: May 8, 2012

(86) PCT No.: PCT/ES2012/070322
§ 371 (c)(1),
(2), (4) Date: Dec. 31, 2014

(87) PCT Pub. No.: WO2013/167761
PCT Pub. Date: Nov. 14, 2013

(65) Prior Publication Data
US 2015/0150439 A1    Jun. 4, 2015

(51) Int. Cl.
| | |
|---|---|
| A61B 1/267 | (2006.01) |
| A61B 1/00 | (2006.01) |
| A61B 1/008 | (2006.01) |
| A61B 1/04 | (2006.01) |
| A61B 1/06 | (2006.01) |
| A61B 1/253 | (2006.01) |
| A61M 16/04 | (2006.01) |

(52) U.S. Cl.
CPC ........ *A61B 1/2673* (2013.01); *A61B 1/00006* (2013.01); *A61B 1/008* (2013.01); *A61B 1/00009* (2013.01); *A61B 1/00032* (2013.01); *A61B 1/00135* (2013.01); *A61B 1/00137* (2013.01); *A61B 1/00154* (2013.01); *A61B 1/00165* (2013.01); *A61B 1/04* (2013.01); *A61B 1/0676* (2013.01); *A61B 1/253* (2013.01); *A61B 1/267* (2013.01); *A61M 16/0488* (2013.01)

(58) Field of Classification Search
CPC .............................. A61B 1/267; A61B 1/2673
See application file for complete search history.

(56) References Cited

U.S. PATENT DOCUMENTS

| | | | |
|---|---|---|---|
| 5,892,630 A | 4/1999 | Broome | |
| 6,878,106 B1 | 4/2005 | Herrmann | |
| 2002/0153008 A1* | 10/2002 | Schwartz | ............. A61B 1/2673 128/200.26 |
| 2010/0168521 A1* | 7/2010 | Acha Gandarias | .. A61B 1/0008 600/188 |

(Continued)

FOREIGN PATENT DOCUMENTS

| | | |
|---|---|---|
| CN | 2588931 Y | 12/2003 |
| CN | 102293632 A | 12/2011 |

(Continued)

OTHER PUBLICATIONS

International Search Report for PCT/ES2012/070322 dated Jan. 29, 2013.

(Continued)

*Primary Examiner* — Olivia C Chang
(74) *Attorney, Agent, or Firm* — Sughrue Mion, PLLC

(57) ABSTRACT

The invention relates to an optical device, sheath and endotracheal intubation system relating to an articulated and reusable optical device, as well as a rigid sheath in which said device is introduced to form the endotracheal intubation system.

28 Claims, 7 Drawing Sheets

(56) References Cited

U.S. PATENT DOCUMENTS

2011/0196204 A1\* 8/2011 Setty ................. A61B 1/00052
600/120

FOREIGN PATENT DOCUMENTS

| | | |
|---|---|---|
| EP | 1 177 809 A1 | 2/2002 |
| EP | 1 647 296 A1 | 4/2006 |
| EP | 1 977 678 A2 | 10/2008 |
| FR | 2821736 A1 \* | 8/2004 |
| GB | 2481515 A | 12/2011 |
| JP | 8-66358 A | 3/1996 |
| JP | 2002-000732 A | 1/2002 |
| JP | 2009-523586 A | 6/2009 |
| WO | 2010/091440 A2 | 8/2010 |
| WO | WO 2011150469 A1 \* 12/2011 ............. A61B 1/267 |

OTHER PUBLICATIONS

Written Opinion for PCT/ES2012/070322 dated Jan. 29, 2013.
Translation of the first communication from the State Intellectual Property Office of the P.R.C. in counterpart application No. 201280074576.1.
Translation of the second communication from the State Intellectual Property Office of the P.R.C. in counterpart application No. 201280074576.1.
Translation of a communication drafted Mar. 15, 2016 from the Japanese Patent Office in counterpart application No. 2015-510844.
Translation of a communication drafted Mar. 9, 2017 from the Japanese Patent Office in counterpart application No. 2015-510844.
Communication from the European Patent Office in counterpart application No. 12 876 322.4.

\* cited by examiner

OPTICAL DEVICE, SHEATH AND ENDOTRACHEAL INTUBATION SYSTEM

CROSS REFERENCE TO RELATED APPLICATIONS

This application is a National Stage of International Application No. PCT/ES2012/070322 filed May 8, 2012, the contents of all of which are incorporated herein by reference in their entirety.

FIELD OF THE ART

The present invention relates to an articulated optical device, a rigid sheath the shape of which adapts to the anatomy of the airway in humans in which said device is inserted, having a common longitudinal axis when they are coupled to one another, and an endotracheal intubation system formed by the articulated optical device and the rigid sheath coupled to one another forming a single functional element. The optical device internally incorporates image transmission means formed by optical components or elements allowing transmitting and therefore viewing the image of the glottis from one end of the device. The articulations of the optical device enable introducing it into the rigid sheath. The assembly of both forms an endotracheal intubation system that can subsequently be introduced into a patient's larynx for viewing the patient's glottis and introducing an endotracheal tube. After using the system in a patient the optical device can be removed from the rigid sheath, the latter can be disposed of for recycling and the optical device used again in a new sheath for a new patient.

The present invention is particularly applicable in the field of medical devices for accessing patient airways and particularly for viewing the glottis and intubating patients.

PRIOR STATE OF THE ART

The applicant is unaware of any system for endotracheal intubation in the state of the art formed by an articulated reusable optical device and a rigid sheath, or of one having the features of the elements described in the present invention or one that comprises the components herein described.

Luminous optical devices comprising at least one viewing conduit which includes at least two reflective elements transmitting the image from one end of the conduit which is introduced in a patient to an image viewer located at the opposite end that remains outside the patient and is where the interior is observed are known in the state of the art. In other words, such devices achieve a clear and sharp image of the image from the distal end thereof (introduced in the patient) to the proximal end thereof (which remains outside the patient and the inside of the patient is observed from this point). To allow said perfect image transmission the viewing conduit internally has at least two elements with reflective surfaces for reflecting the image, located such that they allow perfect image transmission and sharply observing the inside of the patient from the image viewer. It preferably has a set of lenses and/or prisms combined with two reflective surfaces for reflecting the image.

To view the glottis from the outside a patient, specifically from outside the mouth, without needing to hyperextend the neck, the difference in angles between the oral axis and the laryngeal axis must be overcome, this difference of axes being approximately between 60° and 120° when the neck is in the neutral position, i.e., not hyperextended. The three relevant axes when introducing an endotracheal device with the neck in the neutral position are the oral axis, the pharyngeal axis and the laryngeal axis. One such device for working with the neck in the neutral position requires, as mentioned, having a gain in the viewing angle between the oral axis and the laryngeal axis between 60° and 120°. This is because with the neck and head in the neutral position, the angle formed between the oral axis, the pharyngeal axis and laryngeal axis would be approximately between 60° and 120°. In those approximately 60° and 120°, the viewing axis would be formed by the oral axis, the pharyngeal axis and the laryngeal axis and would be located facing the glottis. To overcome this difference in angle between the oral axis and the laryngeal axis in the neutral position, only devices overcoming this difference by means of fiber-optics or by means of placing video cameras at the end of the device that is introduced in the patient, or distal end, which transmit the image by means of a flexible cable from said end to a viewing display located outside the patient, are known in the state of the art.

A device with the aforementioned features is described in international application number WO-2009007478-A1, which mentions the possibility of the device being reusable. Said reusable device comprises two separable parts, a first part corresponding to a first straight segment of the proximal area of the device and comprising the housing for the battery, the first lens, the microcontroller or integrated electronic circuit, electrical conductors and the image viewer, and a second part corresponding to a second straight segment and the curved segment of the device up to its distal area and comprising the lenses behind the first lens, the planar reflective elements reflecting the image, electrical conductors and the illumination device. Said first part and said second part are coupled by means of flanges arranged in the first part that are housed in notches arranged in the second part. Suitable electrical connection elements, preferably jacks, are used for coupling the electrical components, specifically the electrical conductors of the first part and of the second part. The proximal part of the device, including the most contaminating and most expensive elements, can be reused by means of this arrangement and replaced with the distal part which primarily houses most of the lenses and the illumination device.

The preceding reusable device mainly has two drawbacks. The first is establishing leak-tightness of the attachment between the two parts forming the device itself, and the second is that not all the optical and electronic components are reusable, as the non-reusable part, or distal part, comprises lenses and electronic components with a service life at least equal to that of the components present in the proximal part.

In view of the foregoing drawbacks, the applicant has developed an endotracheal intubation system with the features described in the present invention.

DESCRIPTION OF THE INVENTION

As mentioned, the present invention relates to an endotracheal intubation system, comprising an optical device formed by an articulated optical conduit incorporating image transmission means located inside it, and a rigid sheath the shape of which adapts to the anatomy of the upper airway in humans intended for housing the mentioned articulated optical conduit. The upper airway is formed by the upper part of the respiratory tract and in this invention it particularly refers to the buccal cavity or mouth, the pharynx and the larynx to the beginning of the trachea, where the lower airway begins. The nose can also sometimes be considered as part of the upper airway, but it is not included in the present invention. The arrangement of the mouth, pharynx and larynx in humans determines a specific anatomy common to most humans and the shape of the rigid sheath object of the invention adapts to it. The image transmission means can be any means which allow transmitting the image from a distal end of a conduit to at least the opposite proximal end of said conduit. Said transmission means can comprise two reflective surfaces or mirrors combined with other lenses and/or prisms, or a single reflective surface or mirror combined with other electronic devices for transmitting the image, or a fiber-optic cable, among others.

Therefore, a first object of the invention is an articulated optical device according to claim 1.

A second object of the invention is a sheath the shape of which adapts to the anatomy of the airway in humans for removably housing an optical device in an empty conduit, i.e., such that it can be introduced and extracted as many times needed and allows handling the assembly for introducing it into a patient, according to claim 17.

A third and final object of the invention is an endotracheal intubation system according to claim 22.

Therefore, the first object of the present invention is an optical device for viewing the inside of a patient, particularly the glottis, formed by a longitudinal conduit with articulated segments comprising image transmission means and a rigid sheath. The articulated conduit comprises at least two segments or parts attached to one another in an articulated manner, preferably three segments, and separated by an articulation, or two in the case of three segments, which can be integrated at the ends of the segments themselves forming the conduit or be independent from, though associated with, them. The side walls of said conduit are preferably opaque to assure correct image transmission from one end to the other. The distal end of the optical conduit comprises an optical prism with an inclination on one of its surfaces to refract or deflect the image such that the field of view is shifted with respect to the projection of the distal end of the device, i.e., the prism deflects the image of the glottis with respect to a supposed or imaginary extension or continuation of the conduit at its distal end, which therefore allows observing the glottis that is not aligned with the optical conduit when the latter is introduced in the patient inside a sheath. If the optical device is introduced in the patient following the upper airway, the device would be facing the glottis forming the entry point into the endotracheal tube; however, it is necessary to use the mentioned rigid sheath in order to be able to introduce said tube, in addition to maintaining leak-tightness of the optical device, in addition to making the assembly reusable. As mentioned, said sheath has a conduit for introducing the optical device and a canal parallel to the preceding conduit for introducing the endotracheal tube. Since there are two conduits, the optical device is no longer facing the glottis or entry into the trachea, but is slightly shifted towards one side, so the mentioned prism deflecting the image is arranged in order to observe the entry into the trachea through the optical device and enable the subsequent introduction of the tube into the trachea.

As mentioned, the second object of the invention is a rigid sheath in which the optical device is removably introduced and the sheath has an anatomical shape, i.e., a shape following the trajectory of the anatomy of the airway in humans in the neutral or natural position, i.e., without hyperextension, of the patient's neck, and it has a first straight segment and at least one curved segment after the preceding one, its proximal end coinciding with the free end of the first straight segment and its distal end with the free end of the curved segment, said sheath forming an empty conduit closed at its distal end, such that the optical device and the sheath form a single functional assembly when coupled together. The coupling between them is achieved after introducing the optical device into the sheath, which coupling can only be done in a single position to assure leak-tightness of the system and the accurate positioning of all the elements forming the image transmission means to enable correctly viewing the glottis from the proximal end of the system once said endotracheal intubation system is introduced into the patient's airway. Likewise, as a result of using preferably electronic control means, the optical device can only be used when it has been introduced into the sheath.

A final object of the invention is an endotracheal intubation system formed by a rigid sheath and an optical device housed in the sheath.

Once the articulated element is introduced into the rigid sheath, it adopts the shape of the sheath, for which purpose it has two extreme positions, a position in which the articulations are extended or open, facilitating introducing the articulated element into the sheath as it adapts to its anatomical shape, and a position in which the articulations are closed such that the articulated element adapts to the shape of the rigid sheath, adopting the anatomical shape described above.

Said optical device internally incorporates all the electrical, electronic and optical elements, such as reflective surfaces, lenses, prisms, microchips, digital cameras, optoelectronic elements, etc., necessary for transmitting the image from the end of the endotracheal intubation system located inside the patient, or distal end, to the end of the system located on the outside, or proximal end, or to an external monitor through a cable or wireless signal. The optical device can also include other elements such as a light point and a heating system.

In contrast, the sheath only comprises a hollow rigid body with an open end and a closed end, at least one conduit for introducing the optical device into it forming the sheath. At the closed end, distal end, the conduit is closed by a transparent element, window or lens, allowing the optical device to be able to transmit the image of the patient's glottis.

Said sheath can have a canal or guide parallel to the preceding for guiding an endotracheal tube into the patient or a canal serving for aspiration and/or ventilation.

The sheath can also include an additional element, such as a hinged or non-hinged removable cover or protective element to close the proximal end with a transparent element that allows seeing the image from the proximal end.

Therefore, and once the optical conduit is introduced into the sheath, a leak-tight endotracheal intubation system is formed in which there is no risk of contaminating or damaging the optical device or the components included in it due to the patient's internal fluids. After having introduced the sheath and the optical device into the patient, the rigidity of the sheath allows, when the user of the endotracheal intubation system object of the invention moves the proximal end of the sheath with his/her hand or hands, said movements to be transmitted to the distal end located inside the patient.

As mentioned, the optical device incorporates at least one articulation splitting the conduit into two parts or segments, a first straight segment extending from the proximal end and a second curved segment, which can in turn be split into two curved segments with an additional articulation between them. Said articulations allow the different segments of the conduit to form an angle between 90° and 180°, i.e., the longitudinal axis of the straight segment forms an angle between 90° and 180° with the axis passing through the ends of the curved segment, allowing an extended position (180°) which thereby allows being introduced inside the rigid sheath, which has an angle between the longitudinal axis of its straight segment and the axis passing through the ends of the curved segment between 90° and 120°.

As mentioned, the optical device comprises the electrical, electronic, optical, and optoelectronic components, the wiring and, notably, a light point, preferably an LED located at the distal end, and a heating system to prevent the lenses from steaming up, both being controlled and operated by an electrical/electronic system with batteries and operating switch. The heating system arranged at the distal end of the conduit, preferably around the aforementioned prism, must have a sufficient calorific value to heat both the wall of the device as well as the walls and lens or transparent element arranged at the distal end of the sheath, which is slightly inclined to prevent the reflection of the image caused by the light point of the conduit. Said calorific value must also be limited to prevent damaging the walls of both the optical conduit and the sheath. Incorporating all these elements in the optical device allows completely reusing the device on several occasions as it enables use together with different rigid sheaths which, after use and unlike the optical device, are disposable.

Among the optoelectronic components, a sensor which collects and digitizes the image either after this image has gone through a reflective element or has been captured directly, as well as wireless transmission elements for transmitting the image to an external monitor or to any other device can be incorporated.

It should further be pointed out that the segments or parts attached to one another in an articulated manner or articulated segments forming the optical conduit of the device could be articulations or movable mechanical attachments or attachments made of a flexible material, incorporated or not in the segments attached to one another in an articulated manner and in any case allowing angular movement of the relative position of said parts with respect to one another to allow varying their position. In the case of being hinged mechanical attachments, they could be covered with a flexible material to assure the leak-tightness of the inside of the apparatus.

DESCRIPTION OF THE DRAWINGS

For the purpose of aiding understanding of the invention, the following figures attached to the description are referred to below.

DESCRIPTION OF A PREFERRED EMBODIMENT

Figure 1:
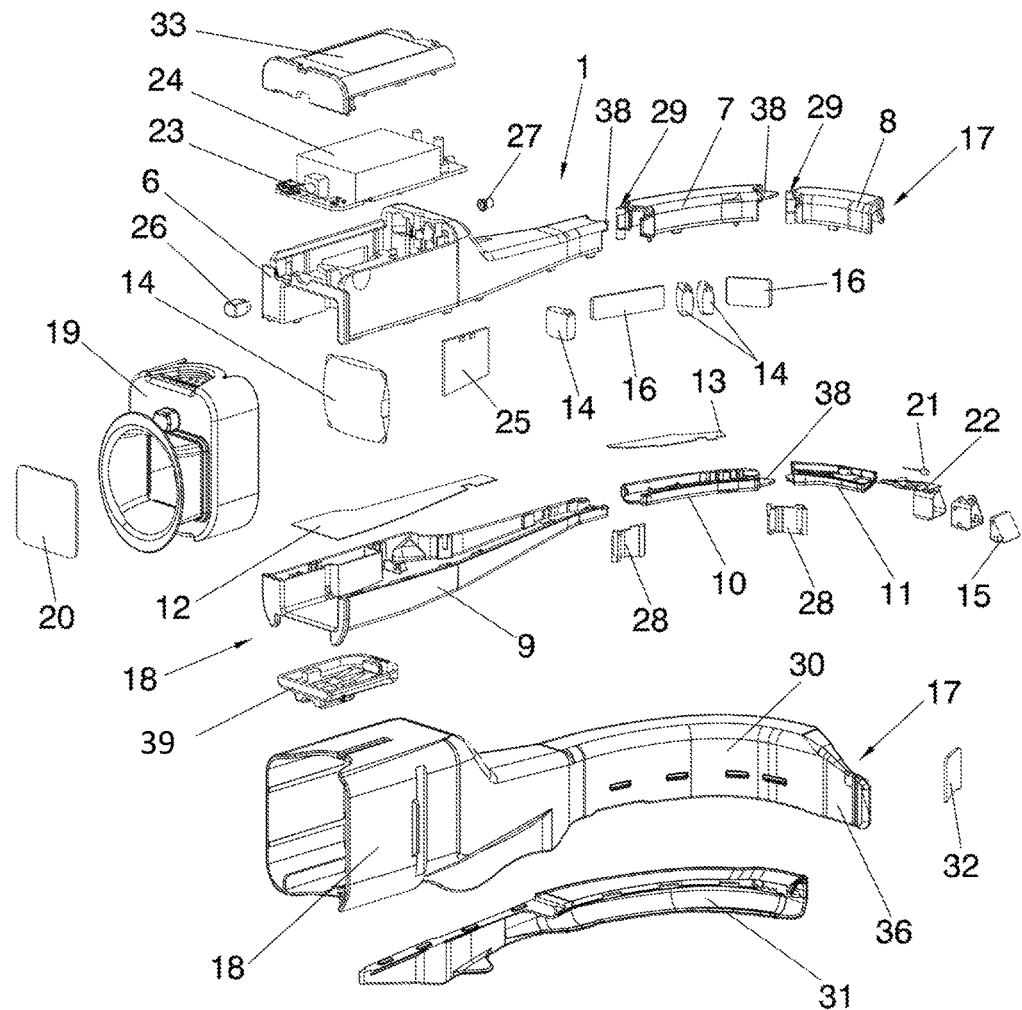
FIG. 1 shows an exploded view of an example of an endotracheal intubation system object of the present invention, where all its components prior to the assembly thereof can be seen.

In view of the mentioned figures and according to the reference numbers used, the figures depict a preferred embodiment of the invention.

It can be seen that the intubation system (1) in question comprises a longitudinal optical device (2) formed by three segments (3, 4, 5) attached to one another and which are in turn formed by respective bases (6, 7, 8) and covers (9, 10 and 11) made of an opaque material to assure image transmission. The optical device (2) forms a conduit that can be internally separated by partitions (12, 13) forming two longitudinal compartments running inside said device. A plurality of lenses (14), prisms (15) and reflective surfaces or mirrors (16) arranged such that they allow transmitting the image from the distal end (17) of said conduit to the proximal end (18) is housed in one of said compartments. The cables communicating the distal end (17) with the proximal end (18) are located in the other compartment, separated by partitions (12, 13).

The cables specifically communicate a light point or LED (21) close to the distal end (17) acting as a light source, as well as a heating element (22) to prevent the lenses from steaming up, with the electro/electronic system located at the proximal end (18), specifically housed in a casing (33) arranged for such purpose at the proximal end of the optical device. Said electro/electronic system comprises at least one main printed circuit board (23) connected to a supply battery (24), an auxiliary printed circuit board (25), a switch (26) and a safety button (27). Said cables can also connect a heating system located at the distal end of the conduit with the preceding electro/electronic components.

Going back to the structure of the optical device (2) and the articulated optical element forming it, it can be seen that the mentioned segments forming it are a straight segment (3) corresponding to the straight segment of the device, and a curved segment. The straight segment forms a first articulated straight part, and the curved segment is preferably formed by a second segment and a third articulated segment, both curved. The first straight segment is attached in an articulated manner to the second curved segment, which is in turn attached in an articulated manner to the third curved segment. It is possible for the curved segment to not be split into two parts, such that the optical conduit would only be formed by a first straight segment and a second curved segment.

The conduit preferably has three segments articulated to one another and the articulated attachment between the different segments is formed by articulation elements integral with but independent of the segments forming the conduit per se. Said articulated attachments can also be incorporated in each of the segments of the optical conduit.

The straight segment (3) coinciding with the first straight part (3) is particularly formed by a proximal base (6) and a proximal cover (9) separated from one another by the first partition (12); and the curved segment is in turn formed by two curved segments, a second curved segment or curved intermediate part (4) and a third curved segment or curved distal part (5). Said curved segments are formed, respectively, by an intermediate base (7) and intermediate cover (10), separated by a second partition (13), and by a distal base (8) and distal cover (11). The straight segment (3), intermediate segment (4) and distal segment (5) are coupled by means of articulated attachments consisting of hinges (29) and parts (28) limiting the rotation of the hinges, allowing only a certain angular movement of the relative position of said segments to vary their position between 90° and 180°. It specifically varies the position between the longitudinal axis of the straight segment and the axis passing through the curved ends of the curved segments, forming two extreme positions, a closed extreme position in which the mentioned axes can form between 90° and 120°, depending on the curvature of the sheath where the optical device will be introduced, and an open extreme position in which the mentioned axes can from 180°, i.e., the axis passing through the ends of the curved segment can be an extension of the longitudinal axis of the straight segment.

In a possible embodiment of the invention, said articulated attachments (28 and 29) are mechanical hinges covered with a joint made of a flexible material (not depicted) to aid with the leak-tightness of the inside of the apparatus, which is assured by the leak-tightness of the rigid sheath in which the optical conduit is introduced. The articulated attachments (28 and 29) alternatively consist of a clamp or similar element made of a flexible material, such as that depicted in the drawings, which can also be in turn covered with a flexible material.

Figure 3:
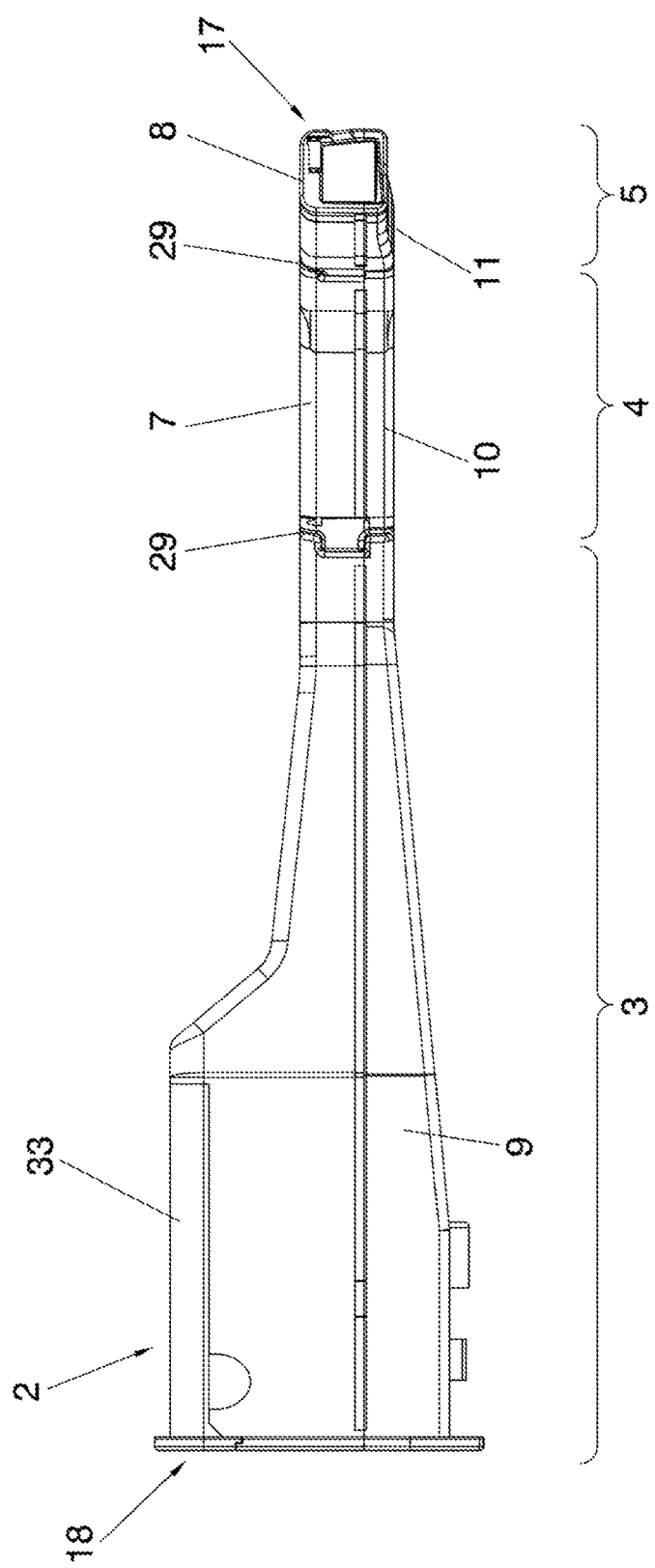
FIG. 3 shows an elevational view of the optical device of the intubation system in its closed position as it would be introduced in the sheath.
Figure 4:
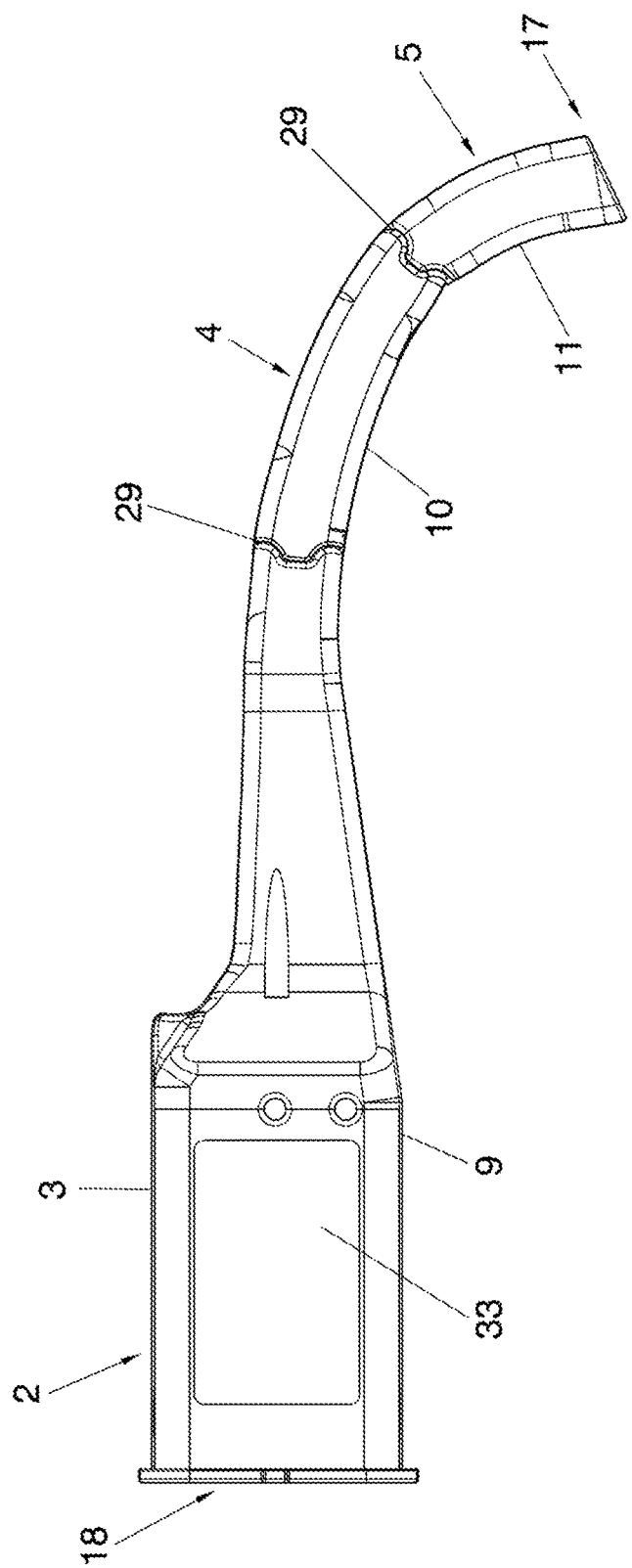
FIG. 4 shows a plan view of the optical device of the intubation system in its closed position as it would be introduced in the sheath.
Figure 5:
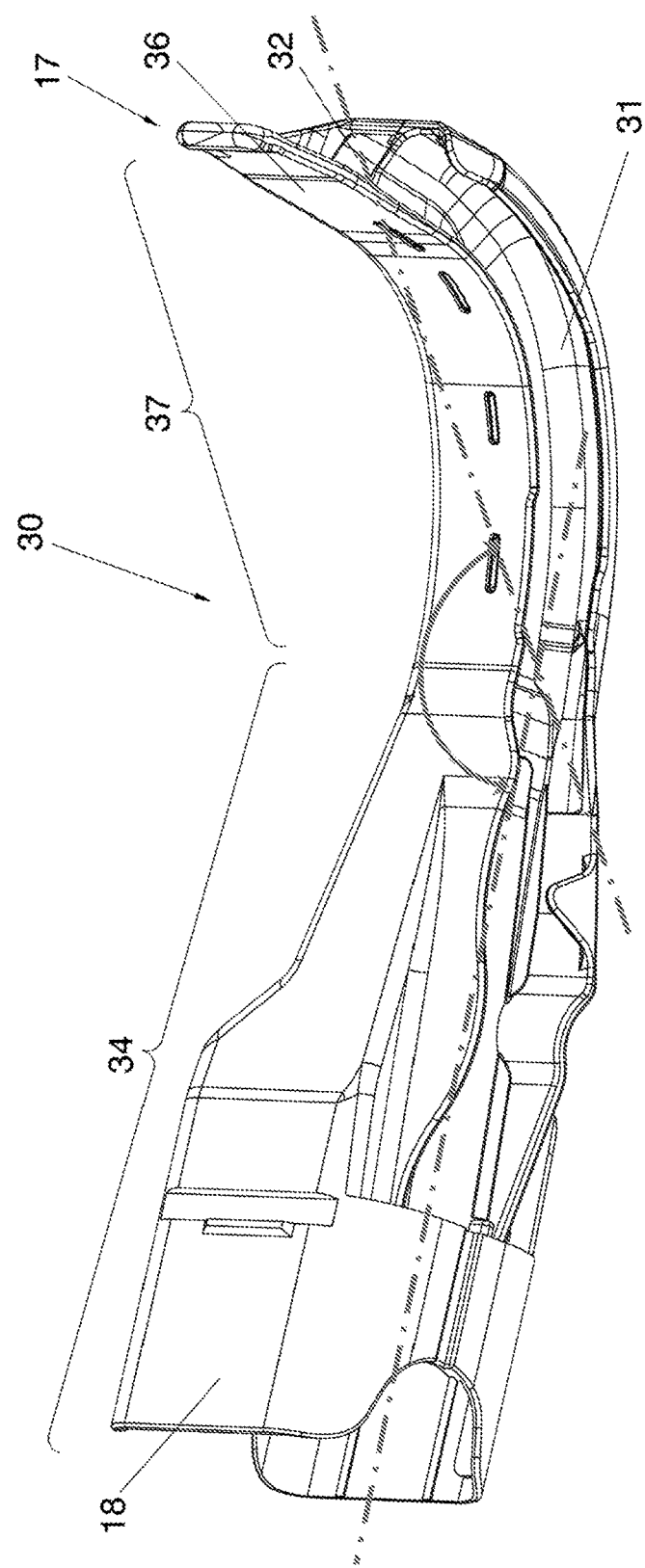
FIG. 5 shows a perspective view of the sheath object of the invention.
Figure 6:
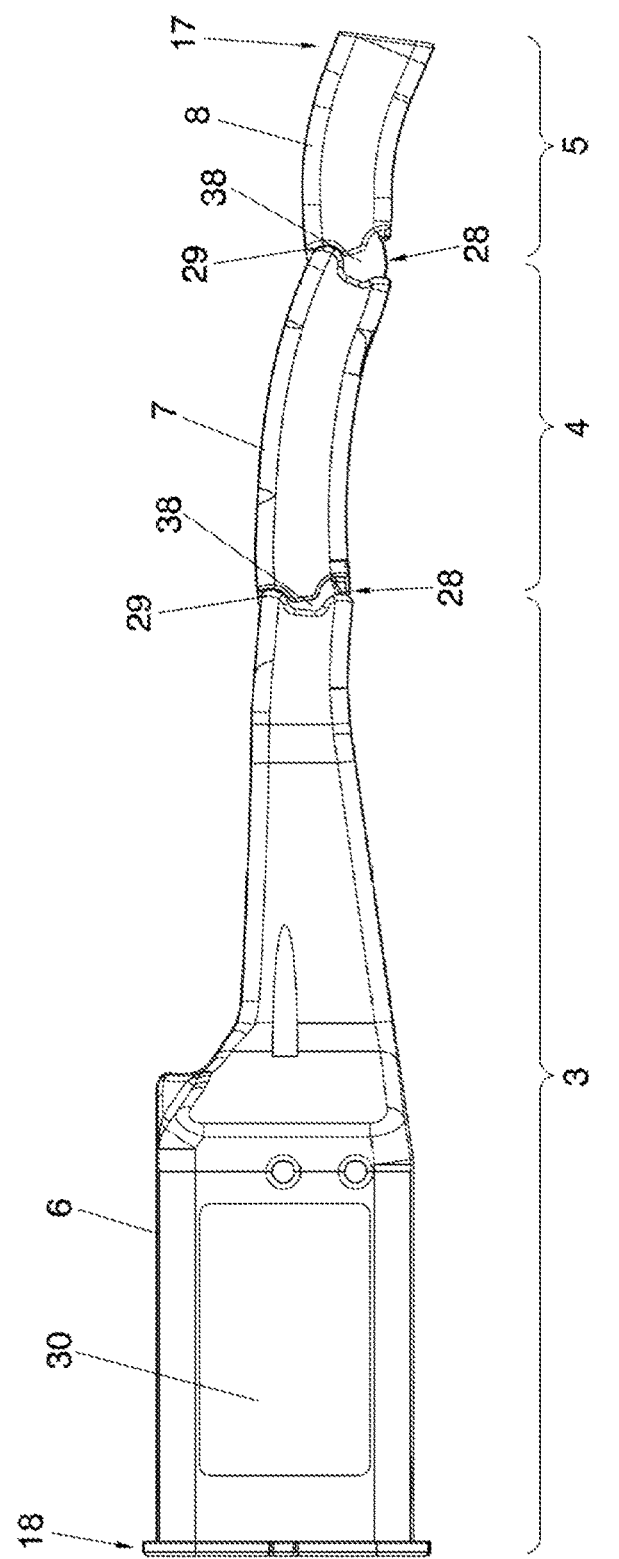
FIG. 6 shows an elevational view of the optical device in its extended position as it would be prior to being introduced in the sheath.
Figure 7:
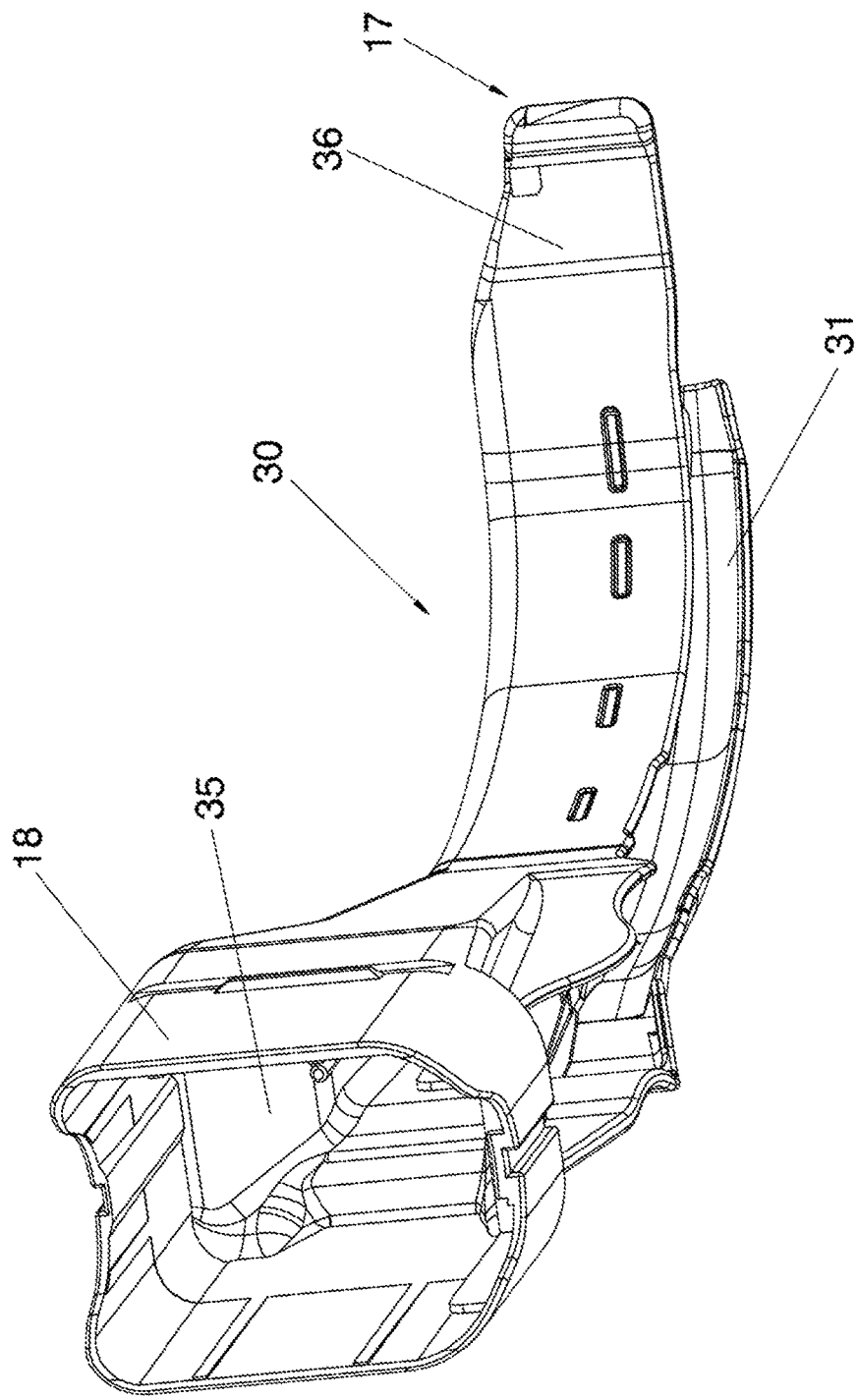
FIG. 7 shows a perspective view of the sheath where the entry conduit of the optical device can be seen.

In the example included in the drawings, the articulations are formed by hinges (29) attaching the different segments (3, 4, 5) of the optical device to one another, specifically said hinges (29) are integrated in the bodies of the proximal base (6), the intermediate base (7) and the distal base (8), such that they allow the movement of one segment with respect to the next one. The proximal base and cover (6, 9) and intermediate base and cover (7, 10) have extensions in their walls at their distal ends which are introduced in the contiguous segment, aiding in maintaining leak-tightness. Said walls are fully introduced in the contiguous segment when the device is closed (FIG. 3) and partially introduced when the optical device is extended (FIG. 5). To prevent opening more than what is necessary, the articulations comprise rotation limiting devices (28) the function of which is, as indicated by the name, to prevent segments from rotating with respect to the other more than what is necessary.

The endotracheal intubation system object of the invention has, in addition to the optical device, a sheath (30) made of a rigid material for removably housing an optical device inside it and it has an anatomical shape, being understood as having a shape following the trajectory of the anatomy of the airway in humans when in the neutral or natural position, i.e., without hyperextension of the patient's neck. The sheath has a straight segment (34) and a curved segment (37) after the preceding one, its proximal end coinciding with the free end of the first straight segment and its distal end with the free end of the curved segment. Said sheath (30) forms a conduit (35) closed at its distal end and open at its proximal end in which said optical device (2) is introduced such that it will adapt to the curvature of the sheath. The distal end of the sheath is closed by a transparent element, or a lens, (32) assuring leak-tightness of the conduit (35) of the sheath (30), and by extension of the optical conduit, and therefore in turn allows transmitting the image of the glottis from the distal end (17) to the proximal end (18) of the optical device (2). Said transparent element is slightly inclined to prevent the reflection of the light emitted by the light point or LED (21) located at the distal end. The angle formed between the axis of the straight segment and the axis passing through the ends of the curved segment is between 90° and 120°, such that the curvature of the sheath (30) coincides with the anatomical curvature of the airway in humans when the neck is not hyperextended, i.e., it is in the neutral or natural position.

As mentioned, the sheath (30) provides additional leak-tightness to the optical device (2), which allows introducing it into the patient without the risk of fluids generated by the patient or arranged on the sheath (lubricants) entering in the optical conduit, affecting the optical elements incorporated therein. By using the sheath (30)m it is possible to reuse the optical device (2) incorporating the elements necessary for viewing the glottis of the patient with a new sheath (30) after having disposed of the previous one.

An articulated cover or protective element or image viewer (19) provided with the corresponding lens (20) and closing the conduit (35) of the sheath (30) at said end is arranged at the proximal end (18) of the sheath.

A canal, conduit or guide (31) is additionally envisaged in the lateral part of the sheath (30), running along it, being suitable for introducing an endotracheal tube, an additional fiber-optic cable, or as an aspiration-ventilation canal.

The sheath (30) has at its distal end a planar area or straight blade (36) for lifting the epiglottis when the intubation system is introduced in the patient, removing it from the field of view and therefore allowing viewing the patient's glottis.

The articulated optical conduit of the optical device (2) includes image transmission means inside it, which means in the present example are formed by optical image transmission elements for transmitting the image from the distal end (17) to the proximal end (18), though they can be replaced with other transmission means, as will be described below. As mentioned, in this example the optical conduit comprises optical elements defining an optical image transmission axis, specifically:

a first lens (14) located at the proximal end of the conduit, at the start of the straight segment, a second lens (14) located approximately at the end of the straight segment, before the beginning of the curved segment, a first reflective element or mirror (16) located before the start of the first curved segment, a third lens (14) located after the first reflective element in the second part, a fourth lens (14) after the third lens, and a second reflective element or mirror (16) located at the end of the curved segment.

The optical axis could be defined as the line that the light follows for transmitting the image from the distal end to the proximal end of the device.

The first and second lenses are located in the first straight segment of the articulated optical conduit, whereas the first reflective element or mirror, the third lens, the fourth lens and the second reflective element or mirror are located in the curved segment of the articulated optical conduit.

A distal optical element (15), preferably a prism, is arranged at the end of the optical conduit, at the distal end (17), allowing the field of view captured by the optical device to be shifted with respect to an extension or imaginary continuation of the optical conduit, and the optical device thereby always focuses on the center of the patient's glottis.

The optical device comprises at its distal end, preferably near the distal optical element (15), a heating element (22) which is connected with the electronic components arranged at the proximal end of the conduit, particularly with the electronic control board (23), and having sufficient calorific value to be able to heat the wall of the optical device, which is in contact with the wall of the sheath (30), as well as said walls and the lens or transparent element (32) located at the distal end of the sheath. The heat produced allows heating the transparent element or lens (32) of the sheath (30) to the human body temperature and therefore prevent the formation of steam which would prevent correct image transmission.

Another alternative construction consists of arranging a fiber-optic cable as image transmission means running through the optical conduit, such that the components necessary for capturing and converting what is captured by the fiber-optics are arranged at the proximal end.

Figure 2:
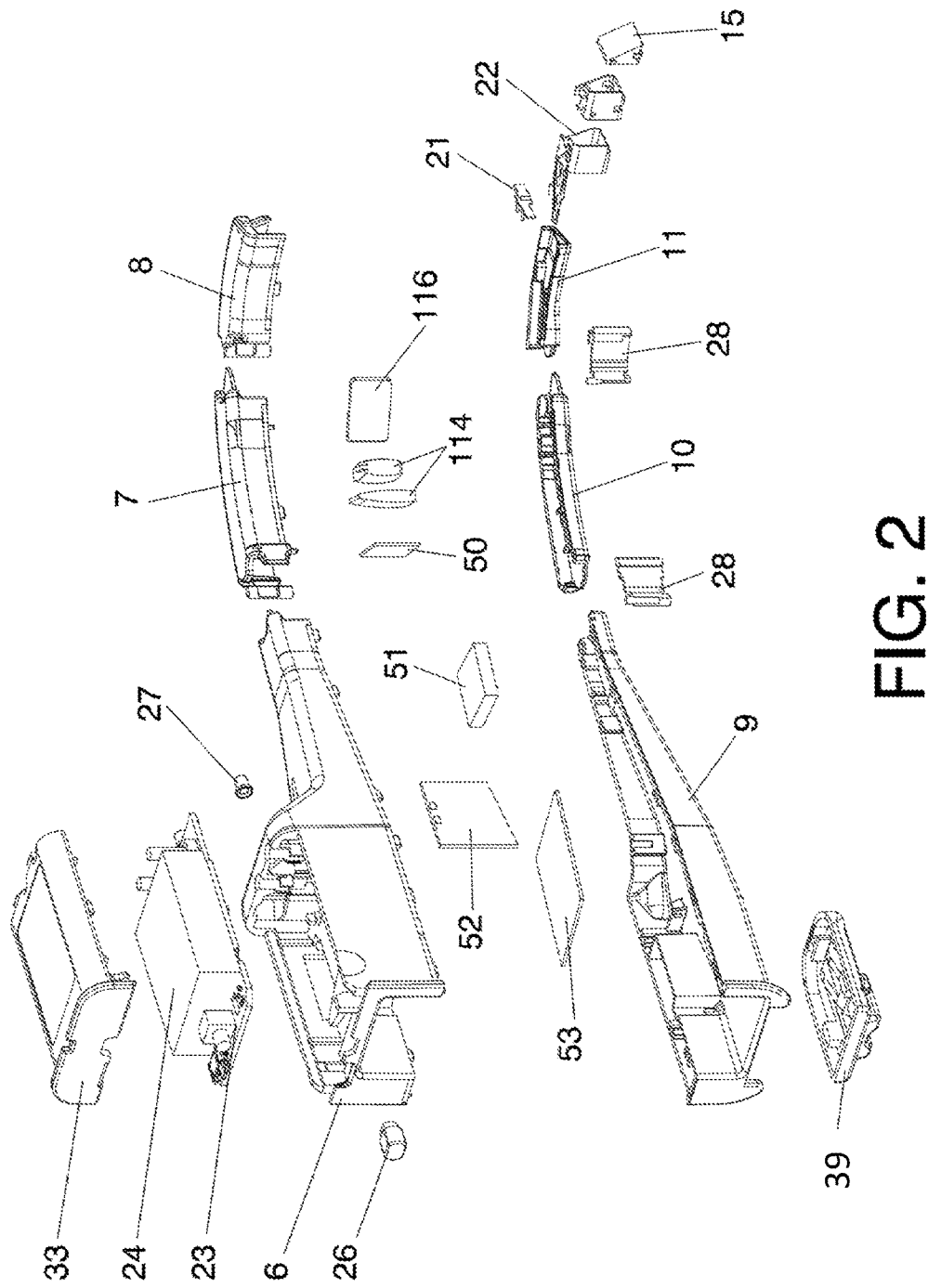
FIG. 2 shows an example of an optical device object of the present invention alternative to that of FIG. 1, and where the common components with the solution of FIG. 1 as well as alternative transmission means with respect to those shown in FIG. 1, can be seen.

FIG. 2 shows an alternative construction of an optical device object of the present invention, in which the aforementioned image transmission means have been replaced with a reflective element or mirror (116) located in the distal curved segment, one or more lenses, preferably two (114), a digital video or image sensor (50) located thereafter which collects and digitizes the image reflected by the reflective element from the distal end (17) of the conduit.

Once the sensor (50) has captured and digitized the video or image, the video or image is transmitted out of the optical device either by means of a cable or by means of a wireless communication module. An image transmission module (51), located after the mentioned sensor (50), and additionally an auxiliary printed circuit board (52) and a printed circuit board (53) for transmitting the image are arranged to process and transmit the image captured by the sensor (50) combined with the aforementioned elements.

In view of the preceding description, to use the endotracheal intubation system it is necessary to introduce the articulated optical device (2) into the conduit of the rigid sheath (30) and subsequently cover the proximal end of the sheath (30) with a protective element, cover or image viewer (19), which can be integrated in an articulated manner in the sheath, such that the optical device is coupled in the sheath, both parts forming a single functional element, and the articulated optical device (2) being isolated from the outside by means of the sheath (30) and the cover, protective element or image viewer (19). Once coupled, the proximal end of the sheath coincides with the free end of the first straight segment of the optical device, and the distal end of the sheath coincides with the free end of the curved segment of the optical device.

A positioning and locking system 39 is arranged between the optical device and the sheath to assure correct positioning and locking of the optical device (2) inside the sheath (30) and to be able to assure that the optical axis is suitably aligned for optimal image transmission between the distal end and the proximal end of the intubation system. Said system consists of mechanical anchors located in the proximal area assuring the suitable relative position of the optical device with respect to the sheath.

Close contact areas have also been provided along the conduit of the sheath (30) intended for receiving the articulated optical conduit of the device (2) to aid in the correct positioning of said device in the sheath, eliminating the degrees of freedom that the articulations confer to the optical device. Specifically, there is a tight fit in the proximal area, the middle area and in the distal area.

Contact elements between optical device and sheath which must precisely fit together and also contribute to assuring the correct positioning and operation of the system are in turn arranged to assure that the optical device, and by extension the intubation system, only works when the optical device and the sheath are coupled together In summary, the system object of the present invention comprises an optical device (2) articulated with an optical conduit formed by a straight segment and a curved segment, with one or two conduits running inside it, image transmission means such as lenses (14) and/or prisms (15) and/or reflective surfaces or mirrors (16) which transmit the image from the distal end (17) to the image viewer (19) of the proximal end (18) being housed in one of them. The intubation system can alternatively have a viewing system comprising an electronic/digital video sensor (50) which collects and digitizes the image located after the image has passed through a reflective element (116) and an element transmitting the digital video signal (51, 52, 53) by means of a connection with or without a cable to an external monitor, also having a light source such as an LED (21) and a heating element (22) operated by an electro/electronic system with a main printed circuit board (23), a battery (24), an auxiliary printed circuit board (25), switch (26) and a safety button (27). The optical device (2) comprises an articulated optical conduit formed by various segments (3, 4, 5) attached to one another by means of articulated attachments (28) allowing certain angular movement of the relative position of such segments to vary their position between 0° and 180°, such that the optical device (2) is introduced in a sheath (30) made of a rigid material, with an anatomical curvature between 90 and 120 degrees, said device (2) adapting to the curvature of said sheath (30).

Having sufficiently described the nature of the present invention as well as the manner of putting it into practice, it is not considered necessary to provide any further explanation so that a person skilled in the art may understand its scope and the advantages derived from it, so the present invention may be carried out into practice through other embodiments differing in detail from that indicated by way of example but within its essential nature.

The invention claimed is:

1. An optical device for viewing an image of a glottis, formed by an optical conduit with a distal end and a proximal end, the optical conduit closed along a path of the conduit so as to define an elongated enclosure between the distal end and the proximal end, wherein the device is articulated and comprises:
   at least two segments, the at least two segments including a proximal segment and a distal segment attached to one another by at least one articulation allowing the movement of one segment with respect to the other between two positions, including a closed position in which the at least one articulation is closed and an open or extended position in which the at least one articulation is open,
   image transmission means housed inside the enclosure to capture and/or transmit the image of the glottis from said distal end, and
   wherein at least one end of the proximal segment or of the distal segment at the at least one articulation comprises an extension configured such that a terminal end of the extension moves within a recess in an opposing end of the other of the proximal segment or of the distal segment when the device is reconfigured between the closed position and the extended position, so as to cover at least in part the at least one articulation and assist in providing leak tightness of the at least one articulation; and wherein the distal segment has a permanently curved shape and the proximal segment has a permanently substantially straight shape.

2. The device according to claim 1, wherein in the closed position the device has a shape following the trajectory of a human airway in the neutral or natural position, wherein the proximal end of the device coincides with a free end of the proximal segment, and the distal end of the device coincides with a free end of the distal segment.

3. The device according to claim 1, wherein in the closed position the device has a shape following the trajectory of a human airway in the neutral or natural position, wherein the proximal segment is substantially straight, the distal segment is curved, and further comprising a second curved segment, the proximal end of the device coinciding with a free end of the proximal segment, and the distal end of the device coinciding with a free end of the curved distal segment, said three segments being attached to one another in an articulated manner.

4. The device according to claim 2, wherein the at least one articulation of the segments of the device allows an angle between a longitudinal axis of the straight proximal segment and an axis passing through a proximal end of the curved distal segment and the free end of the curved distal segment to be between 90° and 120° in the closed position of the device and about 180° in the open position; and wherein the at least one articulation comprises a hinge that limits the allowed angle in the closed position; and wherein angular movement of the at least one articulation is only restricted by the hinge when the device is unsheathed.

5. The device according to claim 1, wherein the image transmission means comprises an optical prism with an inclination on one of its surfaces being located at the distal end of the conduit to refract/deflect the image.

6. The device according to claim 1, comprising at the proximal end of the device an electric power supply unit and an electronic control board connected to one another.

7. The device according to claim 6, comprising a heating element connected with the electronic control board and located at the distal end of the conduit to heat said end as well as any surface in contact therewith.

8. The device according to claim 1, wherein the image transmission means are a fiber-optic cable.

9. The device according to claim 1, wherein the image transmission means are a combination of at least one of lenses and prisms and a reflective element or mirror.

10. The device according to claim 9, comprising optoelectronic elements for digital image capture.

11. The device according to claim 9, wherein the image transmission means are at least a first reflective element or mirror and a second reflective element or mirror located in the distal segment, combined with lenses or prisms located between both reflective elements or between the reflective elements and the free ends of the device.

12. The device according to claim 10, comprising a reflective element or mirror and a digital video sensor located in the distal segment to collect and digitalize the image reflected by the reflective element from the distal end.

13. The device according to claim 12, comprising at least one lens located between the first reflective element and the sensor for correct image transmission.

14. The device according to claim 12, comprising a wireless module located at the proximal end of a cable for transmitting a video signal digitalized by the sensor to an exterior monitor.

15. The device according to claim 1, comprising a lighting element at the distal end connected with an electronic power supply unit.

16. The device according to claim 1, wherein the articulations are covered with a flexible material to assure the leak-tightness of the inside of the conduit.

17. A endotracheal system, comprising the optical device of claim 1 and a sheath for removably housing the optical device of claim 1, wherein the sheath is rigid and twist resistant, and has an anatomical shape following the trajectory of the airway in humans when in the neutral position, with a straight segment followed by a curved segment, a proximal end of the sheath coinciding with a free end of the straight segment and a distal end of the sheath coinciding with an opposite end of the curved segment, forming an empty conduit open at the proximal end and closed at the distal end by a transparent element.

18. The sheath according to claim 17, wherein the angle formed between a longitudinal axis of the straight segment and an axis passing through a beginning of the curved segment after the straight segment and passing through the free end of the curved segment is between 90° and 120°.

19. The sheath according to claim 17, comprising a removable cover or protective element placed at the proximal end to close the conduit of the sheath.

20. The sheath according to claim 17, comprising a straight blade with a planar surface at the distal end.

21. The sheath according to claim 17, comprising a laterally open channel adjacent to the conduit configured to guide or introduce an endotracheal tube.

22. An endotracheal intubation system, comprising the optical device of claim 1 and a rigid sheath forming a conduit closed at one end and open at an opposite end such that the device is removably introduced in the sheath through the open end.

23. The system according to claim 22, wherein the sheath is twist resistant and has an anatomical shape following the trajectory of the airway in humans when in the neutral position, with a straight segment followed by a curved segment, a proximal end of the sheath coinciding with a free end of the straight segment and a distal end of the sheath coinciding with an opposite end of the curved segment, forming an empty conduit open at the proximal end and closed at the distal end by a transparent element.

24. The system according to claim 22, wherein once the optical device and the sheath are coupled, the distal end of the sheath coincides with the free end of the second segment of the optical device.

25. The system according to claim 22, comprising a single positioning and locking system located between the optical device and the sheath to assure the correct coupling between both during use.

26. The system according to claim 22, comprising close contact areas between the outside of the optical device and the inside of the sheath to assure the correct positioning of the optical device in the sheath.

27. The system according to claim 22, comprising contact means between the sheath and the power supply unit of the device to activate the power supply unit of the device, assuring correct positioning of the device in the sheath and the operation of the optical device exclusively when the optical device is inside the sheath and correctly positioned.

28. The device according to claim 1, further comprising a rigid sheath configured to removably house the at least two segments and image transmission means, the sheath has an anatomical shape generally following a shape following the trajectory of a human airway in the neutral or natural position and including a straight segment followed by a curved segment.

* * * * *